United States Patent [19]
Zavracky et al.

[11] Patent Number: 5,705,424
[45] Date of Patent: Jan. 6, 1998

[54] PROCESS OF FABRICATING ACTIVE MATRIX PIXEL ELECTRODES

[75] Inventors: Paul M. Zavracky, Norwood; Duy-Phach Vu, Taunton; Brenda Dingle, Mansfield; Matthew Zavracky, North Attleboro; Mark B. Spitzer, Sharon, all of Mass.

[73] Assignee: Kopin Corporation, Taunton, Mass.

[21] Appl. No.: 215,555

[22] Filed: Mar. 21, 1994

Related U.S. Application Data

[63] Continuation-in-part of PCT/US93/08601, Sep. 10, 1993, which is a continuation-in-part of Ser. No. 944,207, Sep. 11, 1992, Pat. No. 5,444,557.

[51] Int. Cl.$^6$ .............. H01L 21/20; H01L 21/22; H01L 21/304; H01L 21/52
[52] U.S. Cl. .............. 437/86; 437/90; 437/181; 437/208; 437/915; 437/974; 359/90; 345/92
[58] Field of Search .............. 437/86, 90, 181, 437/208, 915, 974; 148/DIG. 135, DIG. 150; 359/90; 345/92

[56] References Cited

U.S. PATENT DOCUMENTS

| | | | |
|---|---|---|---|
| 4,024,626 | 5/1977 | Leupp et al. | 29/571 |
| 4,429,305 | 1/1984 | Hosokawa et al. | 340/784 |
| 4,727,047 | 2/1988 | Bozler et al. | 437/89 |
| 4,740,782 | 4/1988 | Aoki et al. | 340/719 |
| 4,770,498 | 9/1988 | Aoki et al. | 350/334 |
| 4,808,983 | 2/1989 | Banjamin et al. | 340/719 |
| 4,838,654 | 6/1989 | Hamaguchi et al. | 350/333 |
| 4,935,792 | 6/1990 | Tanaka et al. | 357/23.7 |
| 4,952,031 | 8/1990 | Tsunoda et al. | 350/342 |
| 4,965,565 | 10/1990 | Noguchi | 340/784 |
| 5,020,881 | 6/1991 | Matsuda et al. | 350/333 |
| 5,056,895 | 10/1991 | Kahn | 359/87 |
| 5,073,772 | 12/1991 | Takafuji et al. | 340/784 |
| 5,095,304 | 3/1992 | Young | 340/766 |
| 5,117,298 | 5/1992 | Harai | 359/55 |
| 5,166,816 | 11/1992 | Kaneko et al. | 257/59 |
| 5,184,235 | 2/1993 | Sukegawa | 359/60 |
| 5,191,453 | 3/1993 | Okumura | 359/59 |
| 5,206,749 | 4/1993 | Zavracky et al. | 359/59 |
| 5,256,562 | 10/1993 | Vu et al. | 437/86 |
| 5,258,320 | 11/1993 | Zavracky et al. | 437/40 |
| 5,285,517 | 2/1994 | Wu | 385/142 |
| 5,317,236 | 5/1994 | Zavracky et al. | 315/169.3 |
| 5,376,561 | 12/1994 | Vu et al. | 437/31 |
| 5,377,031 | 12/1994 | Vu et al. | 359/59 |
| 5,444,557 | 8/1995 | Spitzer et al. | 359/59 |

FOREIGN PATENT DOCUMENTS

| | | |
|---|---|---|
| 0 248 905 | 12/1987 | European Pat. Off. |
| 0 474 474 A3 | 3/1992 | European Pat. Off. |
| 0 486 318 A1 | 5/1992 | European Pat. Off. |
| 63-55529 | 3/1988 | Japan |
| 63-101830 | 5/1988 | Japan |
| 62-38727 | 2/1989 | Japan |
| 1-195421 | 8/1989 | Japan |
| 92/12453 | 7/1992 | WIPO |

OTHER PUBLICATIONS

Laakso et al., "A 9 Inch Diagonal, Compact, Multicolor TFEL Display", 1991 International Display Research Conference, pp. 43–44.

Sumiyoshi et al. "Device layer Transferred Poly Si TFT Array For High Resolution Liquid Crystal Projector" IEDM, (1989) pp. 165–168.

Matsumoto et al. "Liquid Ctystal Displays (LCD)" In Electronic Display Devices (John Wiley & Sons) (1984) pp. 29–84.

*Primary Examiner*—David Graybill
*Attorney, Agent, or Firm*—Hamilton, Brook, Smith & Reynolds, P.C.

[57] ABSTRACT

The present invention relates to methods of fabricating pixel electrodes for active matrix displays including the formation of arrays of transistor circuits in thin film silicon on an insulating substrate and transfer of this active matrix circuit onto an optically transmissive substrate. An array of color filter elements can be formed prior to transfer of the active matrix circuit that are aligned between a light source for the display and the array of pixel electrodes to provide a color display.

22 Claims, 12 Drawing Sheets

PROCESS OF FABRICATING ACTIVE MATRIX PIXEL ELECTRODES

RELATED APPLICATIONS

This is a continuation-in-Part Application International Application No. PCT/US93/08601 filed on Sep. 10, 1993 which is a Continuation-in-Part of U.S. Ser. No. 07/944,207 filed Sep. 11, 1992, now U.S. Pat. No. 5,444,557, the contents of which are incorporated herein by reference.

BACKGROUND OF THE INVENTION

Active matrix displays are being developed which utilize liquid crystals or electroluminescent materials to produce high quality images. These displays are expected to supplant cathode ray tube (CRT) technology and provide a more highly defined television picture. The most promising route to large scale high quality liquid crystal displays (LCDs), for example, is the active-matrix approach in which thin-film transistors (TFTs) are co-located with LCD pixels. The primary advantage of the active matrix approach using TFTs is the elimination of cross-talk between pixels, and the excellent grey scale that can be attained with TFT-compatible LCDs.

Flat panel displays employing LCDs generally include five different layers: a white light source, a first polarizing filter that is mounted on one side of a circuit panel on which the TFTs are arrayed to form pixels, a filter plate containing at least three primary colors arranged into pixels, and finally a second polarizing filter. A volume between the circuit panel and the filter plate is filled with a liquid crystal material. This material will alter the polarization of light in the material when an electric field is applied across the material between the circuit panel and a ground affixed to the filter plate. Thus, when a particular pixel of the display is turned on, the liquid crystal material adjusts light being transmitted through the material so that it will pass through the second polarizing filter.

The primary approach to TFT formation over the large areas required for flat panel displays has involved the use of amorphous silicon which has previously been developed for large-area photovoltaic devices. Although the TFT approach has proven to be feasible, the use of amorphous silicon compromises certain aspects of the panel performance. For example, amorphous silicon TFTs lack the frequency response needed for large area displays due to the low electron mobility inherent in amorphous material. Thus the use of amorphous silicon limits display speed, and is also unsuitable for the fast logic needed to drive the display.

Owing to the limitations of amorphous silicon, other alternative materials include polycrystalline silicon, or laser recrystallized silicon. These materials are limited as they use silicon that is already on glass which generally restricts further circuit processing to low temperatures.

Thus, a need exists for a method of forming high quality TFTs, driver circuits, and electrodes at each pixel of a panel display having the desired speed and providing for ease and reduced cost of fabrication.

SUMMARY OF THE INVENTION

The present invention relates to panel displays and methods of fabricating such displays using thin-films of single crystal or essentially single crystal silicon in which transistors are fabricated to control each pixel of the display. These methods are used to fabricate transmissive displays such as liquid crystal projection displays, or alternatively, for emissive displays including eletroluminescent (EL) displays, both of which can be used for a variety of applications including head mounted displays.

For a preferred embodiment, the thin-film or transistor array is transferred onto an optically transmissive substrate such as glass or transparent plastics. The transfer process typically involves attaching a transparent substrate to the circuit with an adhesive and removing the semiconductor substrate from the silicon-on-insulator (SOI) structure on which the SOI structure containing the circuit is formed. In this embodiment, the thin-film single crystal silicon is used to form a pixel matrix array of thin-film transistors which actuate each pixel of an LCD. CMOS circuitry that is highly suitable for driving the panel display can be formed in the same thin-film material in which the transistors have been formed. The circuitry is capable of being fully interconnected to the matrix array using thin-film metallization techniques without the need for wires and wirebonding.

The pixel electrodes formed in the active matrix display are made from a transparent conductive material such as indium tin oxide, or other metal oxides such as titanium dioxide or zinc oxide. Conductive nitrides, such as altiminium nitride, for example, can also be used. These electrodes can, in certain preferred embodiments, be formed prior to transfer of the circuit onto a transparent substrate. Alternatively, in other preferred embodiments, the pixel electrodes can be formed after transfer of the active matrix circuit onto a transparent substrate. In these latter embodiments vias are formed through the insulating layer on which the transistor circuits are formed to conductively connect the pixel electrodes to their respective switching transistors. This also permits the electrodes to be fabricated over the transistor circuits.

Another preferred embodiment of the invention includes the fabrication of color filter elements to form a color display. The color filter elements are preferably formed prior to transfer and are thus fabricated on the same side of insulating layer as the pixel electrodes, or alternatively, on the opposite side of the insulating layer as the pixel electrodes, or in a third alternative, are formed on the optically transmissive substrate prior to transfer of the circuit onto the substrate. The color filter elements can include blue, green and red regions of polyimide or other suitably pigmented material formed in a pattern that is aligned with the pixel electrode array in the resulting display device. Alternatively, a substractive color display can be formed using color filter elements having cyan, magenta and yellow pigments.

This structure for the color filter system permits the color filter elements to be placed in close proximity to the pixel electrodes. For transmissive systems in which the light is not highly collimated and the pixel size is small, that is, having a pitch between 10 microns and 100 microns and preferably in the range between 10 microns and 30 microns, it is desirable to minimize the distance between the filter element and the corresponding pixel electrode to reduce the propagation of off-axis light from a given pixel electrode through the filter element of a neighboring pixel. In the present system, the color filter elements are placed directly on the pixel electrode material, or alternatively, are positioned at a distance in the range of 1–10 microns from the pixel electrode, preferably in the range of 1–4 microns.

DETAILED DESCRIPTION OF PREFERRED EMBODIMENT

Figure 1A:
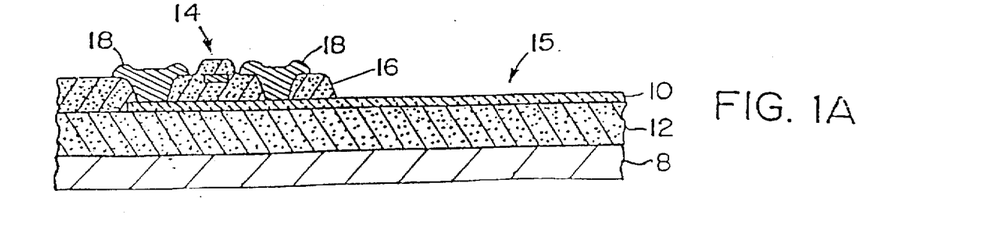
FIGS. 1A–1D illustrate a fabrication sequence of a preferred method of forming an active matrix liquid crystal display.
Figure 1B:
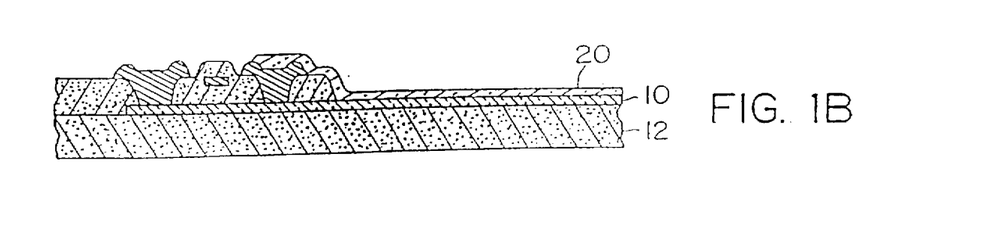
Figure 1C:
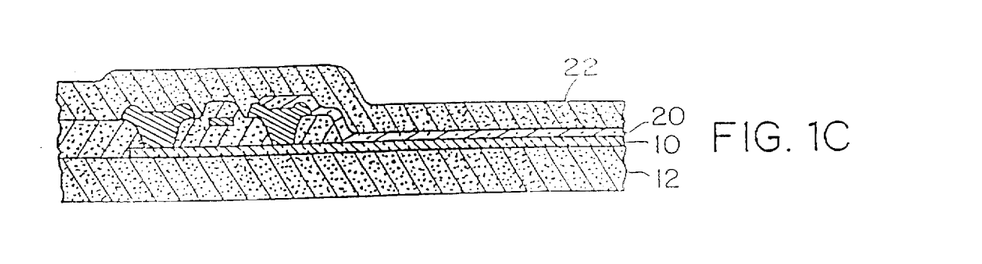
Figure 1D:
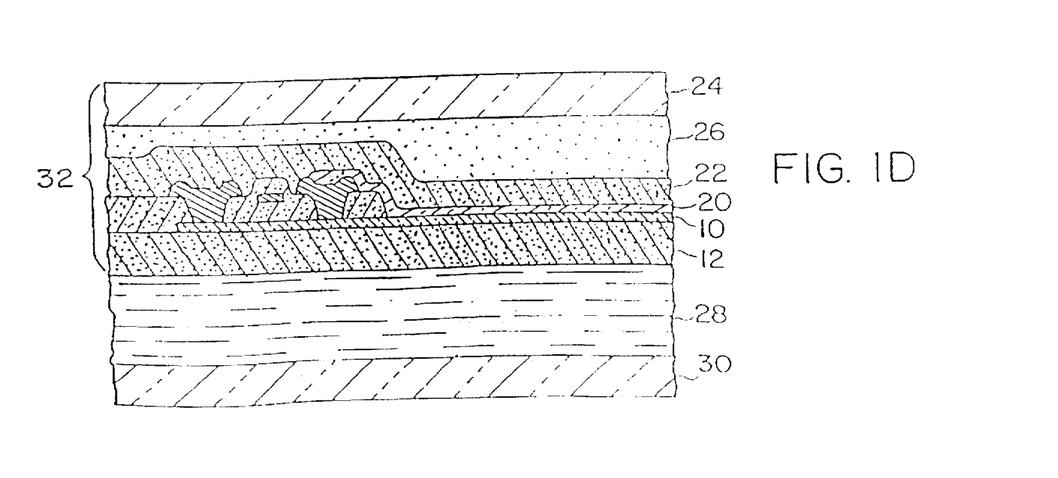

A preferred embodiment of the invention is illustrated in the process flow sequence of FIGS. 1A–1D. As described in detail in U.S. Pat. No. 5,206,749, the contents of which are incorporated herein by reference, active matrix circuits for electronic displays can be fabricated in thin film single crystal silicon and transferred onto glass substrates for display fabrication. In FIG. 1A a transistor 14 in an active matrix circuit has been formed with a thin film single crystal silicon layer 10 over an insulating substrate 12. The areas or regions 15 of the circuit in which pixel electrodes are to be formed are subjected to a silicon etch to expose the underlying oxide and as illustrated in FIG. 1B a transparent conductive pixel electrode 20 is then formed on or over the exposed oxide with a portion of the deposited electrode extending up the transistor sidewall 16 to the contact metalization 18 of the transistor 14. A passivation layer 22 (FIG. 1C) is then formed over the entire device, which is then transferred to an optically transparent substrate 24 as shown in FIG. 1D. A transparent adhesive 26 as described in greater detail in U.S. Pat. No. 5,256,562, the contents of which are incorporated herein by reference, is used to secure the circuit to the substrate 24. The composite structure 32 is then attached to a counterelectrode 30 and polarization elements (not shown) and a liquid crystal material 28 is then inserted into the cavity formed between the oxide layer 12 and the counterelectrode 30.

The above process offers several advantages including reduction of optical transmission losses that occur when using a silicon pixel as described in U.S. Pat. No. 5,206,749, while at the same time using the smallest number of processing steps necessary to produce a dependable device with high yields and which are compatible with other processing requirements.

Figure 2A:
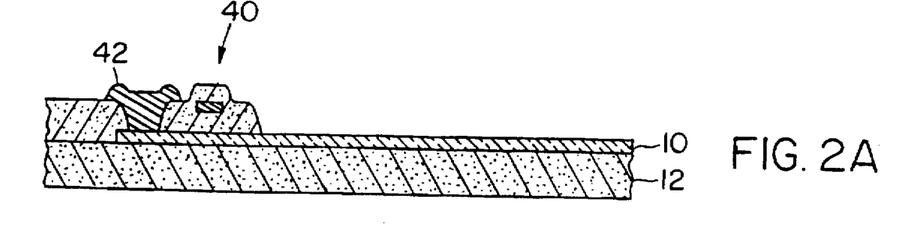
FIGS. 2A–2D illustrate a process sequence for forming the pixel electrodes of an active matrix display.
Figure 2B:
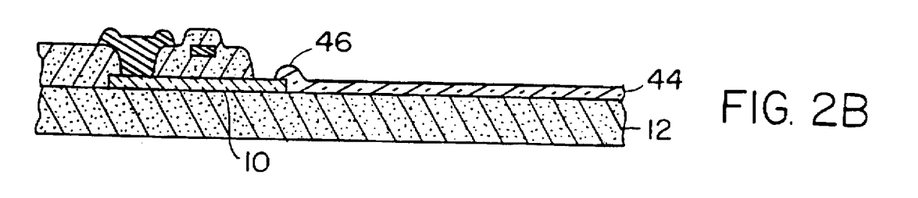
Figure 2C:
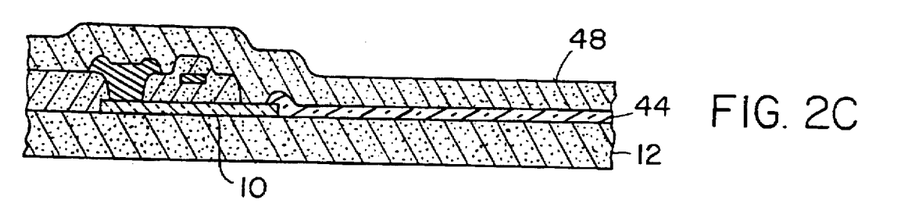
Figure 2D:
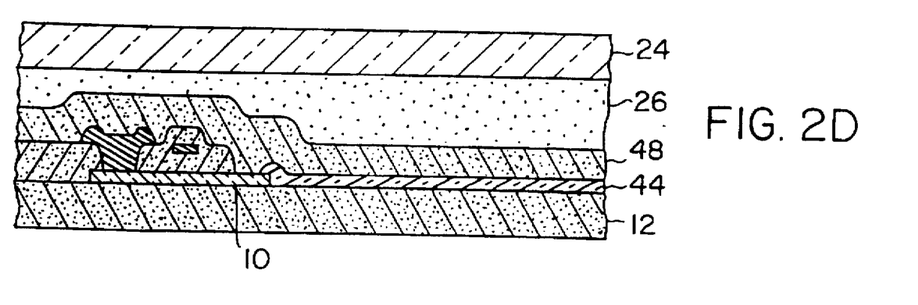

Another preferred embodiment of the invention is illustrated in the process sequence of FIGS. 2A–2D. As in FIG. 1A, an array of transistors 40 is formed using a portion of the single crystal silicon layer 10. In this embodiment, only the data line metalization 42 is formed. As shown in FIG. 2B, a portion of the single crystal silicon of the transistor 40 is masked and the silicon area of each pixel electrode is removed to expose the underlying oxide 12. The mask (not shown) is removed and the transparent conductive electrode 44 such as indium tin oxide (ITO) is deposited with a contact region 46 being in direct contact with the single crystal silicon. A low temperature oxide 48 is then formed on the circuit for passivation as shown in FIG. 2C and the device transferred onto a glass or plastic substrate 24, as shown in FIG. 2D, where an adhesive 26 is used to bond the active matrix circuit to the substrate 24.

As described in previously incorporated U.S. Pat. No. 5,206,749, the active matrix transistor circuits are formed in a single crystal silicon material having a silicon-on-insulator (SOI) structure prior to transfer. The SOI structure can be fabricated using a number of techniques including recrystallization of non-single crystal silicon that has been deposited on a silicon dioxide layer formed on a single crystal silicon substrate (not shown in the figures for clarity). This silicon or other semiconductor substrate can be removed by etching after bonding of the circuit to transparent substrate 24. Other methods for SOI structure fabrication including the bonding of two wafers with an adhesive and lapping of one wafer to form a thin film and transfer of the thin film onto glass, or alternatively by implantation of oxygen into a silicon wafer, can also be used.

Figure 3:
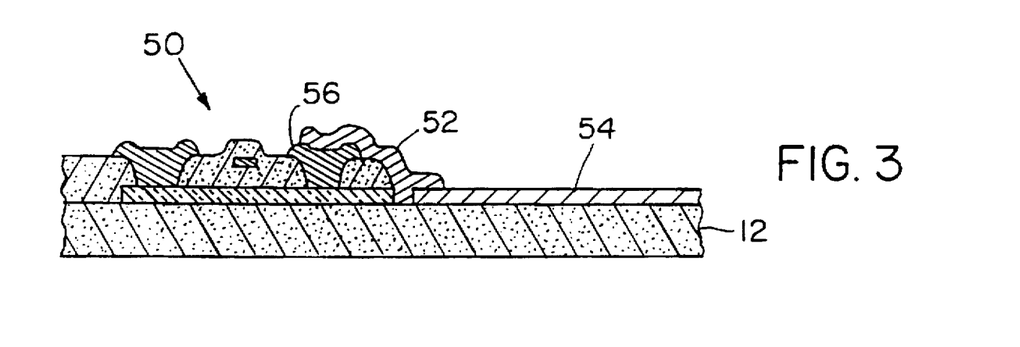
FIG. 3 illustrates another preferred embodiment of a contact to a pixel electrode for a liquid crystal display.

FIG. 3 illustrates a pixel electrode connection to the transistor 50 in which a second metalization 52 is used to connect the transparent conductive pixel material 54 to the transistor electrode metalization 56.

Figure 4A:
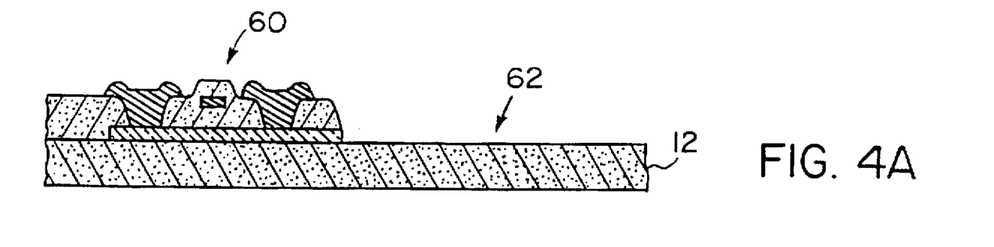
FIGS. 4A–4D illustrate another preferred method of forming the pixel electrodes of an active matrix display.
Figure 4B:
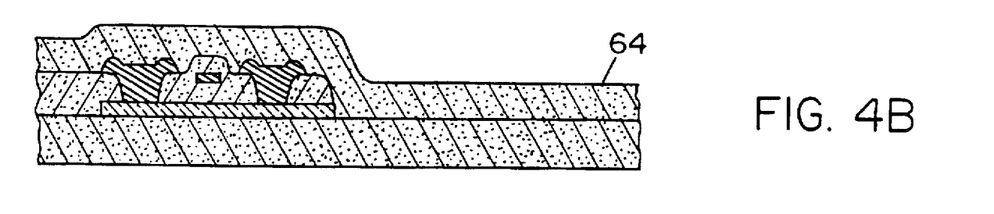
Figure 4C:
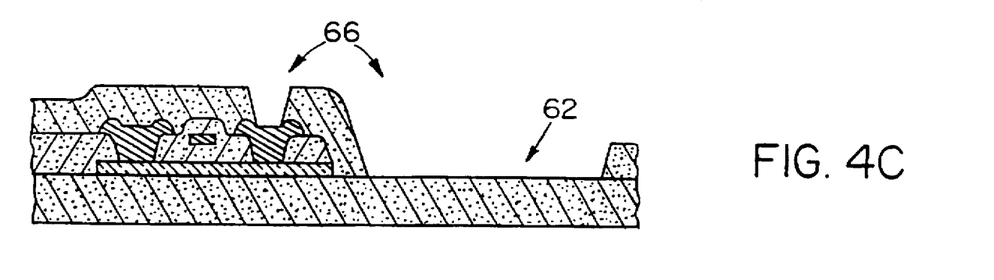
Figure 4D:
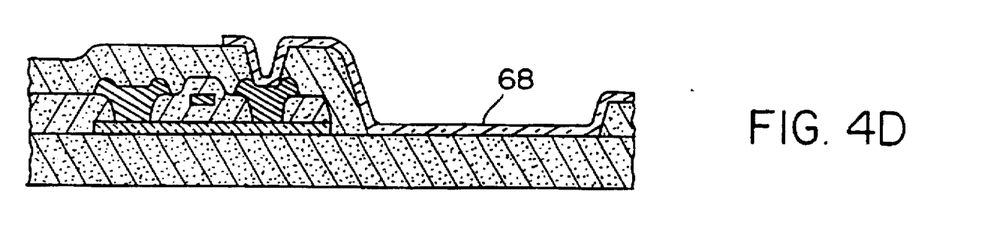

Another preferred embodiment for the fabrication of transmissive pixel electrodes is illustrated in the process sequence of FIGS. 4A–4D. FIG. 4A shows a cross-sectional view of the transistor 60 circuit after removal of silicon from the pixel electrode area 62. In FIG. 4B a low temperature oxide layer 64 is deposited before fabrication of the pixel electrode. In FIG. 4C the passivation layer is cut 66 to expose the transistor metalization for the pixel electrode as well as to expose the pixel electrode area 62. The conductive transmissive pixel electrode 68 is then formed, as shown in FIG. 4D, to cover the pixel electrode area, a portion of the passivation layer, and in contact with the exposed transistor metalization. The electrode 68 can cover all or a portion of the transistor area which is useful for EL display fabrication.

Figure 5:
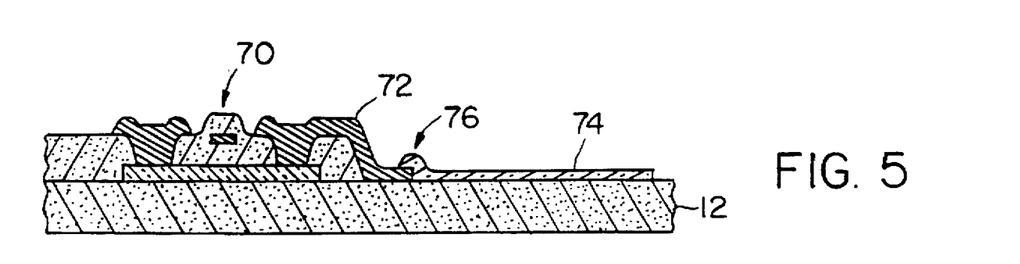
FIG. 5 illustrates a cross sectional view of a preferred embodiment of the invention in which the transistor contact extends to contact the pixel electrode.

Another preferred method of fabricating a conductive transparent pixel electrode is shown in FIG. 5. In this embodiment the pixel electrode metalization 72 to the transistor 70 extends off the transistor circuit area onto or over the exposed oxide 12. The transparent pixel electrode material 74 contacts the metalization in an offset contact area 76. A passivation layer (not shown) is formed after deposition of the pixel electrode material 74. As discussed hereinafter, an electroluminescent material and/or color filter elements can be fabricated over the pixel electrodes in this and other embodiments described herein, and the resulting display circuit transferred onto a second substrate when desired.

Figure 6A:
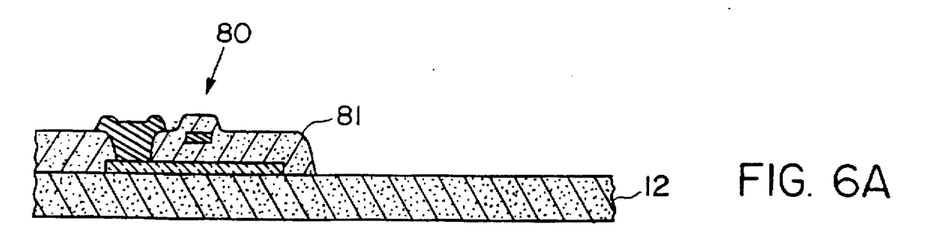
FIGS. 6A–6D illustrate a process sequence in which the pixel electrode material directly contacts the semiconductor source or drain region.
Figure 6B:
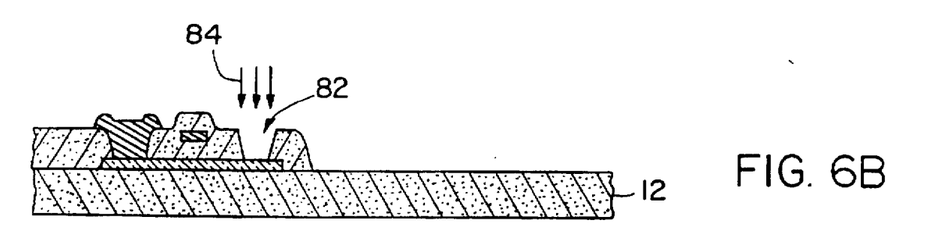
Figure 6C:
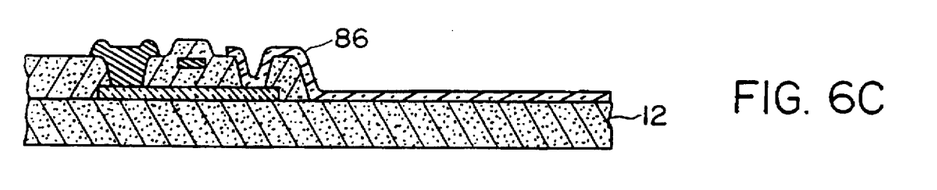
Figure 6D:
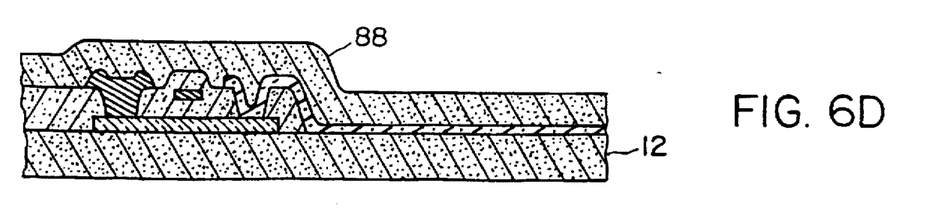

Another preferred embodiment is shown in the process sequence of FIGS. 6A–6D. In this embodiment, the circuit 80 is prepared through data line metalization as shown in FIG. 6A. A via 82 is opened through the oxide layer 81 to the single crystal silicon material (FIG. 6B). The via openings for each transistor circuit in the matrix are then prepared for pixel electrode material deposition by either a sputter etch, a surface treatment 84 of the silicon using a palladium or platinum chloride, or alternatively, by deposition of a thin nickel layer. The pixel electrode material 86, which in the example is ITO, is formed on or over the prepared surface of the silicon exposed by the via (FIG. 6C), followed by the deposition of the passivation layer 88 (FIG. 6D).

Figure 7:
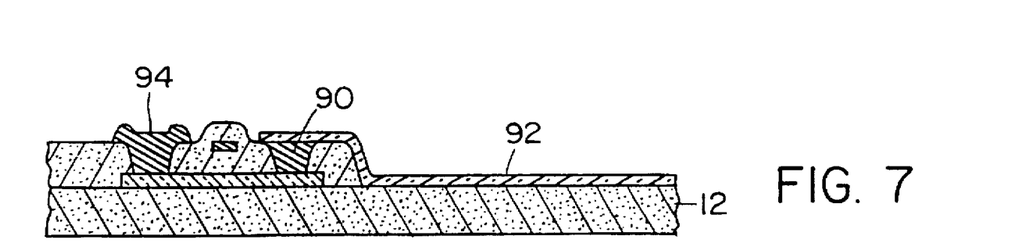
FIG. 7 is a cross sectional view in which the transistor contact to the pixel electrode fills a via through an insulating layer.

FIG. 7 illustrates an embodiment similar to that formed in FIGS. 6A–6D except that the via is filled with deposited metal plug or contact filler 90. The filler can be an electroless plated nickel or be formed by chemical vapor deposition of a metal such as tungsten in a step separate from the formation of the other transistor contact. This is followed by deposition and patterning of an ITO electrode 92 on or over the filler 90, the transistor sidewall and the pixel electrode area. This process provides for use of a different material for the pixel electrode contact than that used for data line metalization. This provides improved conduction to the ITO electrode material.

Figure 8A:
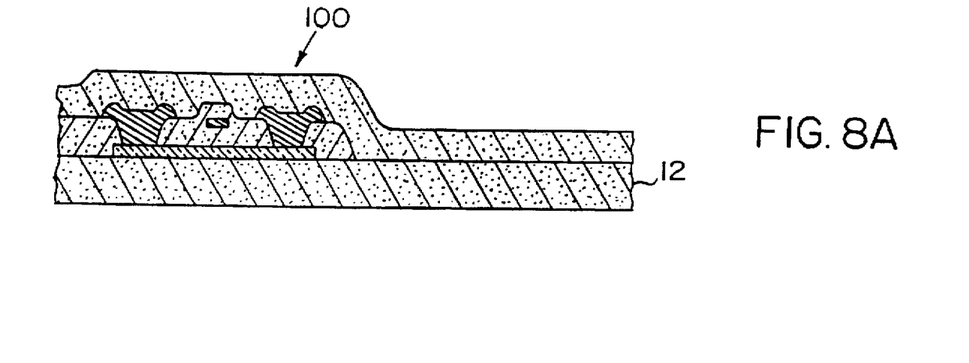
FIGS. 8A–8D illustrate a process sequence in which the pixel electrodes are formed after transfer of the active matrix circuit.
Figure 8B:
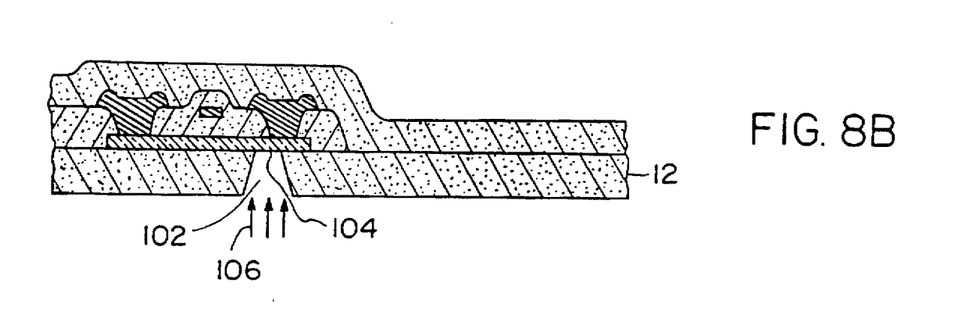
Figure 8C:
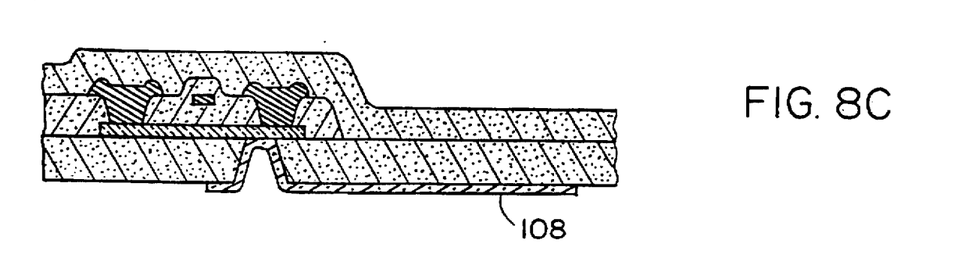
Figure 8D:
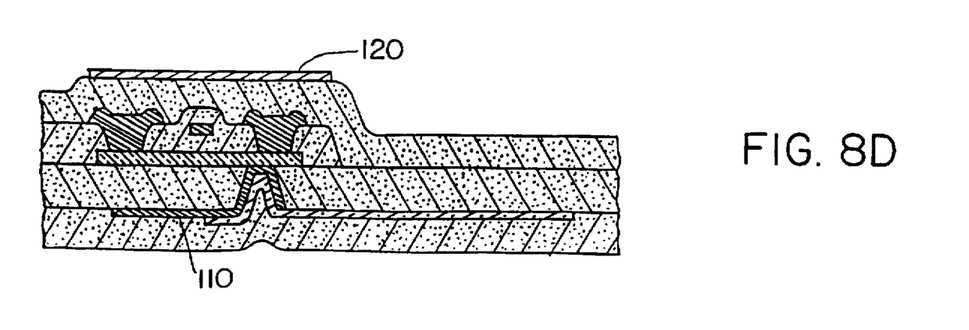

Additional preferred embodiments of the invention involve processes for fabricating active matrix pixel electrodes after transfer of the active matrix circuit onto a transparent a substrate and exposure of the backside of the insulator on which the thin film single crystal silicon was formed. A process sequence illustrating this embodiment is shown in FIGS. 8A–8D. Note that the transfer substrate is used but not shown in the figures for clarity. In this process a transferred active matrix circuit is prepared as shown in FIG. 8A. A via 102 is formed through the insulator 12 to expose a contact area 104 of the silicon in the transistor circuit as shown in FIG. 8B. Surface treatment 106 of the exposed silicon as described previously can be applied if needed, also as shown in FIG. 8B. A conductive transparent electrode material 108 is then deposited and patterned to make electrical contact to the transistor circuit through the via 102 and simultaneously form the pixel electrodes (FIG. 8C). As shown in FIG. 8D, an additional metal layer 110 or other conductive material can be formed between the electrode material 108 and the contact area 104 to improve conductivity. Layer 110 can also act as an opaque light shield on one side of the transistor circuit. A separate light shield region 120 can also be formed on the second side of the circuit in a manner similar to that described in greater detail in U.S. Pat. No. 5,256,562, the contents of which were previously incorporated by reference.

Figure 9A:
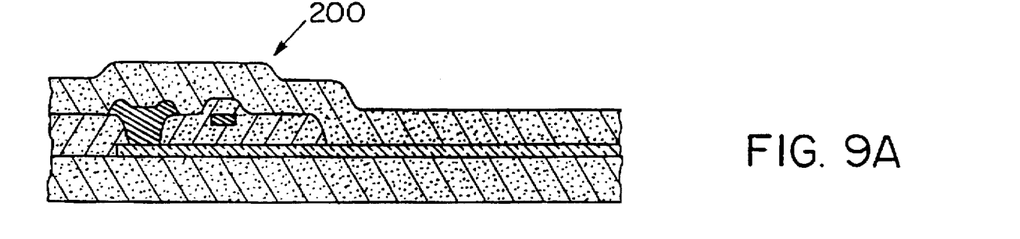
FIGS. 9A–9E illustrate a process sequence in which regions of the insulating layer are removed after transfer to define the pixel electrode regions.

Another preferred embodiment of the invention is described in connection with FIGS. 9A–9E. A transferred circuit 200 is shown in FIG. 9A. The pixel electrode area is defined by the removal of the insulator region 210 and the contact area 215 is defined by via 230 shown in FIG. 9B. The single crystal silicon is removed from the exposed pixel electrode area 220 in FIG. 9C, and the via 230 to the transistor circuit is optionally treated 240 as shown in FIG. 9D. The transparent pixel electrode material 250 is then formed in the via 230 and the pixel electrode area 220 as shown in FIG. 9E. The device is now ready for final display fabrication as described previously.

Figure 9B:
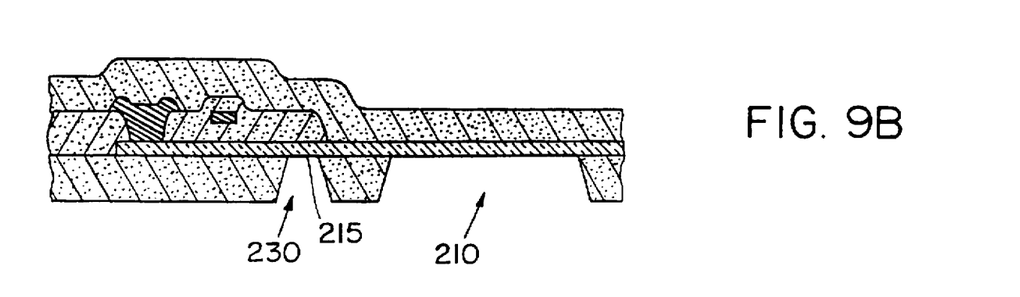
Figure 9C:
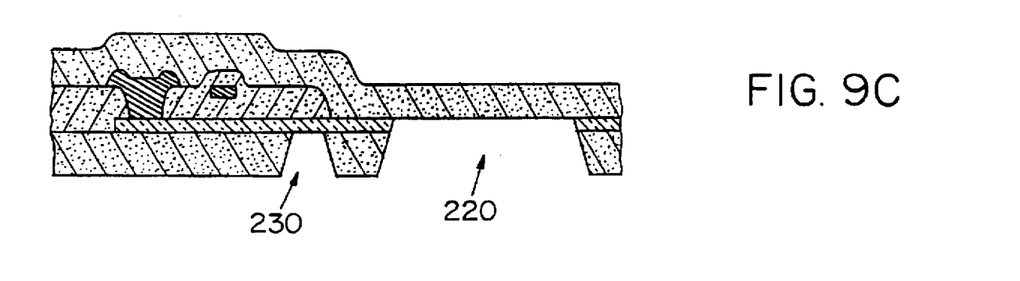
Figure 9D:
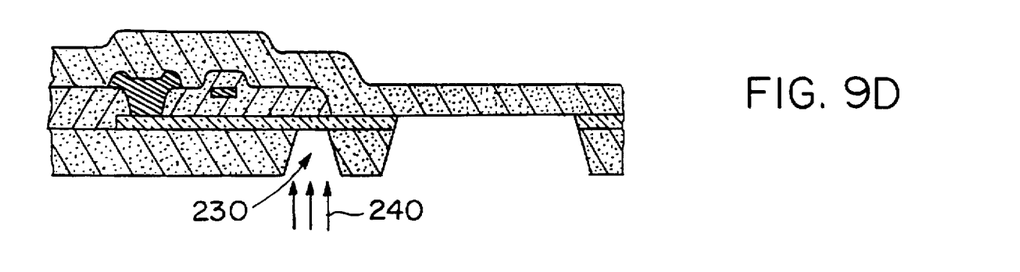
Figure 9E:
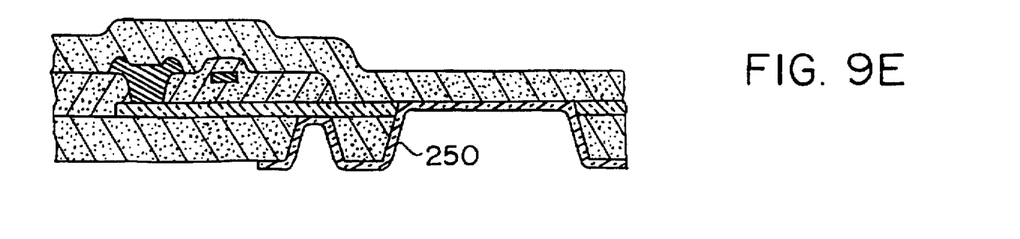
Figure 10A:
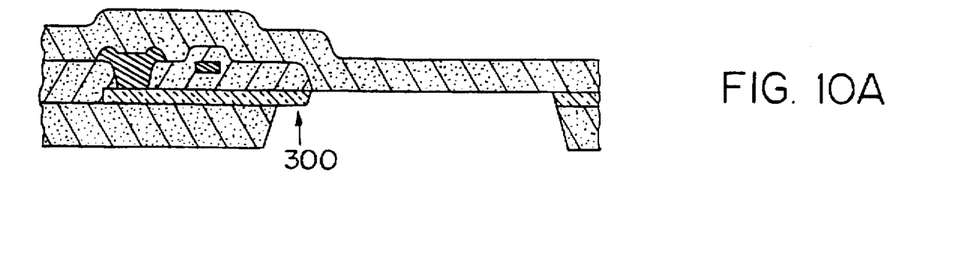
FIGS. 10A–10B illustrate another preferred process for fabricating pixel electrodes after transfer.
Figure 10B:
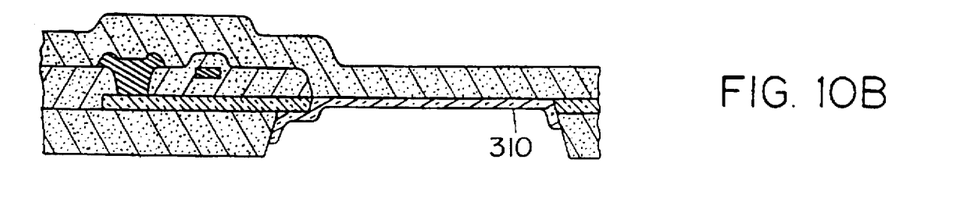

A further embodiment shown in FIGS. 10A–10B involves exposing a portion 300 of the single crystal silicon layer in which the transistor circuit is formed in the step shown in FIG. 9B, and masking the portion of the circuit during removal of the silicon to form the structure shown in FIG. 10A. The conductive transparent electrode 310 is formed as shown in FIG. 10B that can directly contact the transistor circuit at contact area 300, or the exposed silicon can be treated prior to contact formation as described previously. A further passivation layer (not shown) can also be added to cover the pixel electrode 310 to provide electrical isolation, and planarization of the pixel area.

Figure 11A:
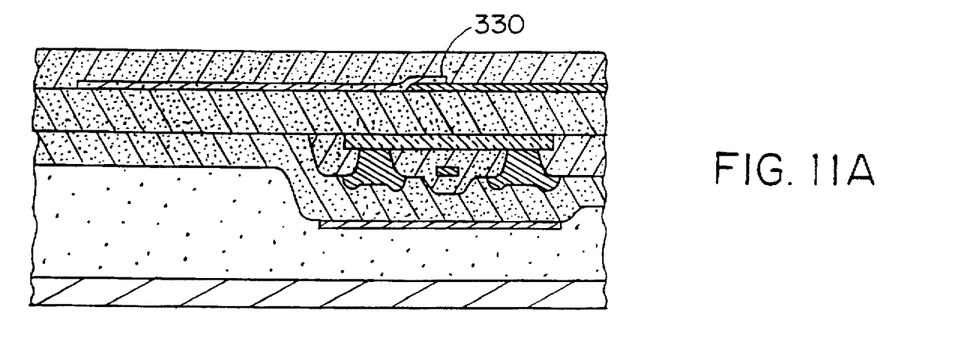
FIGS. 11A–11B illustrate a fabrication process for titanium dioxide pixel electrodes
Figure 11B:
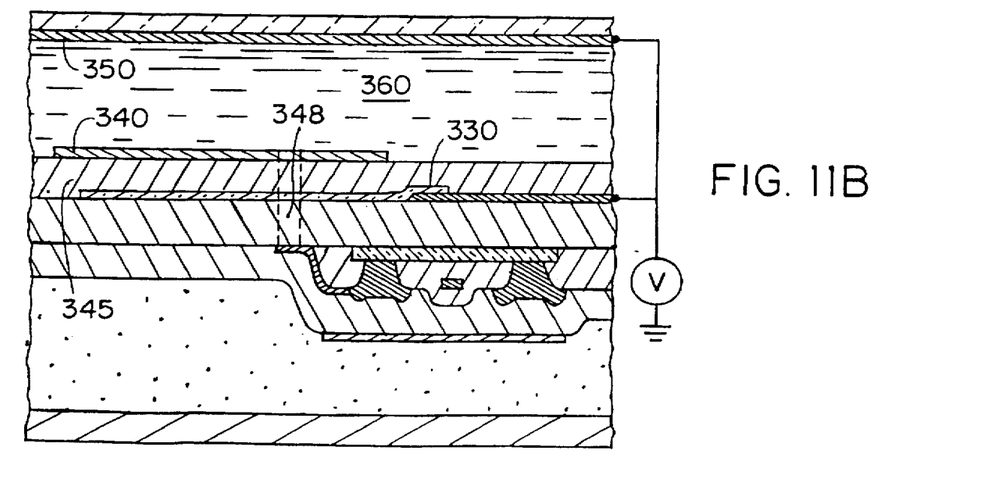

As pixel areas have become smaller, the use of more resistive metal oxides having more suitable optical properties for transmissive displays has become a possibility. Metal oxides such as zinc oxide, titanium oxide, and tin oxide having transmissivities of 99% can be used rather than ITO even though the resistivities of these materials can be 10–1000 times that of ITO. The fabrication of a titanium dioxide pixel electrode is shown in FIGS. 11A–11B. This process or other metal oxides or metal nitrides can be used in any of the processes described elsewhere herein for forming pixel electrodes after or during transistor fabrication. In this process two electrode layers 330, 340 are formed which are separated by an insulator 345. First layer 330 acts as a ground plane and is electrically connected to the electrode 350 on the opposite side of the liquid crystal material 360. This structure provides improved electrical isolation for the pixel electrode 340 that actuates the pixel element. An interconnect 348 is used to connect electrode 340 to the transistor in an area outside of the region occupied by electrode 330. Color filters can be used in this embodiment as well.

FIGS. 12A–12E illustrate another preferred process flow sequence for fabrication of a color filter system that can be used without limitation, for example with transmissive displays, emissive displays, head mounted displays or projection displays. In particular, the color filters are polyimide color filters. More specifically, the color filter illustrated is a "PiC Green 02" polyimide filter material available from Brewer Science, Inc. of Rolla, Mo. Blue and red filter materials are also available from the same source and use substantially the same processing sequence as described hereinafter. As described elsewhere herein, other color separation and selection techniques can also be employed that are compatible with conventional semiconductor photolithography and processing methods.

Figure 12A:
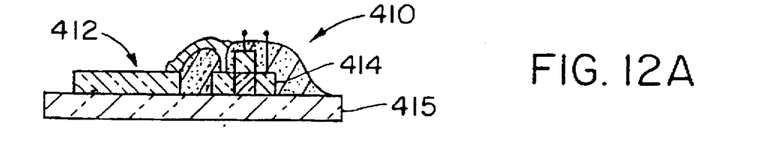
FIGS. 12A–12E illustrate a process sequence for fabricating color filter elements on an active matrix circuit.
Figure 12B:
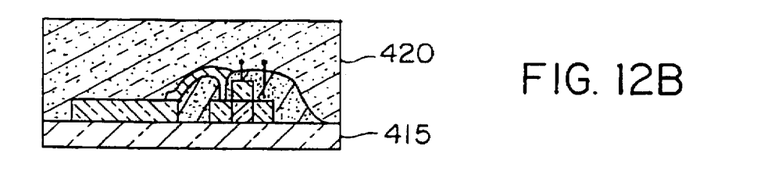

As shown in FIG. 12A, a pixel element 410 having an electrode 412 and a transistor 414 is formed on an insulating layer 415. An optional nitride layer 420 can be formed over the pixel element 410, as shown in FIG. 12B. An optional adhesion promoter (not shown) can next be coated and baked onto the nitride layer 420. The adhesion promotor can be "APX K-1", also provided by Brewer Science, Inc., which can be spun onto the wafer at 5000 RPM, and then baked in an oven. In a preferred embodiment, however, an adhesion promoter is not used.

Figure 12C:
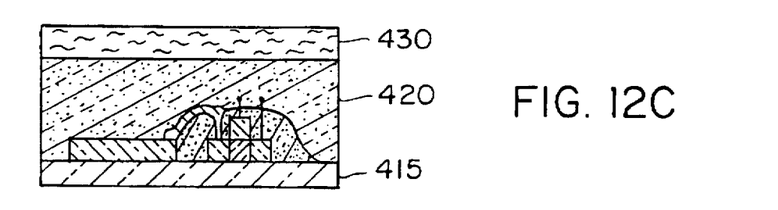

A layer of polyimide, such as "PiC Green 02" is spun on over the circuit at a speed of 1000–4000 rpm for 90 seconds. The resulting structure is shown in FIG. 12C. The polyimide layer 430 is about 0.5 to 5 microns thick. In a preferred embodiment, the polyimide layer 430 is about 1 to 2 microns thick. The structure is then subjected to a solvent removal bake at 120° C. for 60 seconds on a hotplate for example. It should be noted that the particular conditions of the solvent bake are not critical. The structure is then subjected to a second or "beta" bake at 175° C. on a hotplate for 90 seconds in vacuum contact. It is critical that the temperature be uniform in the beta bake step because the beta bake defines the develop processing characteristics.

Figure 12D:
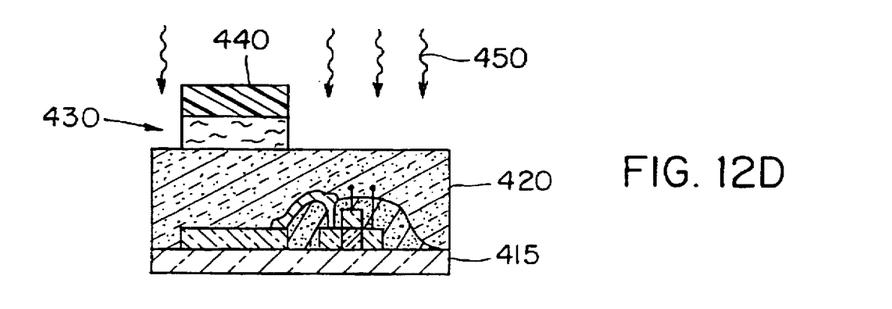

As shown in FIG. 12D, a photoresist pattern 440 is applied to the structure. The positive photoresist is coated, baked and exposed to ultraviolet light 450 using a mask (not shown) at 1.5 to 2 times the normal dosage. The pattern is then developed with a standard fluid developer for 40 seconds. The developer is preferably a metal ion free developer such as "Shipely MF-312". The polyimide 430 will develop with the photoresist. The structure is then rinsed in water and dried with nitrogen or clean compressed air.

Figure 12E:
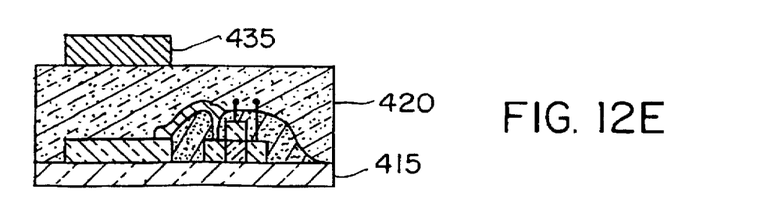

The photoresist 440 is then removed with a commercially available carbon based solvent, such as "Safestrip" from Brewer Science, Inc., which is spun onto the structure. The resulting color filter structure 435 shown in FIG. 12E is then hard baked between 200° and 280° C. for one hour in an oven. In a preferred embodiment, the baked temperature is 230° C.

The above process is repeated for the red and the blue color filters to provide a full color liquid crystal display or EL display. The spin speed and bake temperature are varied as needed depending upon the size of the color filter element. After the color filter elements are completed, the resulting structure is encapsulated using a layer of silicon nitride, oxynitride or silicon oxide. An optically clear polyimide layer can also be used for encapsulation and planarization. The circuit can then be transferred onto a second substrate in accordance with previously described procedures depending upon the type of display being fabricated.

Another preferred embodiment uses red, blue, and green polyimides which incorporate photosensitive material. In this embodiment, the polyimides are put on, exposed and developed. No photoresist is needed using this process. In another preferred embodiment, a filter fabrication process using negative photoresist materials is employed to form an array of color filter elements.

To form a first color filter on each pixel electrode, a pigment is dispersed in a negative resist material and applied as a film. Such colored negative photoresist materials are commercially available. A portion of the film is exposed to light. The remainder of the film is masked (not shown) such that it is not exposed to the light. The exposed portion of the film is developed the presence of the light to form a first color filter element. The undeveloped portion of the film is removed, leaving a pattern of first color filter elements adjacent to each pixel electrode. Second and third color filter elements are formed in a similar manner as the first color filter elements.

Optionally, a matrix array of opaque (or black) elements can be formed over or adjacent the transistor region of each pixel electrode as well as over the interprise spaces. Each opaque element serves to absorb light and provide a uniform background.

In other preferred embodiments, a color filter array is formed adjacent to the active matrix circuitry by applying a color photographic development process for each color which uses color-coupler containing developers.

A black and white silver halide emulsion layer is formed adjacent to each pixel electrode of the active matrix. The formation of color filter elements utilizing a silver halide emulsion can be reviewed in greater detail in U.S. Pat. No. 4,400,454. An isolation layer such as $SiO_2$, is formed over the active matrix and patterned to expose the portion of the emulsion layer adjacent each pixel electrode. This portion of the emulsion layer is exposed to light to provide silver particles. A first developer containing a color coupler is added to each exposed region of the emulsion layer. As such, a dye of a first color is then formed in each region. Next, the silver is removed by bleaching or rehalogenating for each region.

Portions of the unexposed silver halide emulsion layer electrode adjacent to each pixel are then exposed to light through a patterned isolation layer formed over the active matrix. A second developer containing a color coupler is added to each exposed region of the emulsion layer to form a dye of a second color in each region. Next, the silver is removed by bleaching or rehalogenating for each region.

The remaining portions of the unexposed silver halide emulsion layer adjacent to the pixel electrodes are then exposed to light through a patterned isolation layer. A third developer containing a color coupler is added to each exposed region of the emulsion layer to form a dye of a third color in each region. Next, the silver is removed by bleaching or rehalogenating for each region. The isolation layer is removed and any silver halide remaining in the emulsion layer is removed by fixing. An array of color filter elements are thus formed adjacent to each pixel electrode.

Alternatively, a color filter array can be formed by applying a color photographic development process which uses developers containing dye developers. To accomplish this, the above-described process is performed using developers containing dye developers instead of developers containing color couplers. After processing such as that described in the Figures the thin film with the formed color filter elements can than be transferred, if necessary, for further processing prior to final display fabrication.

Figure 13A:
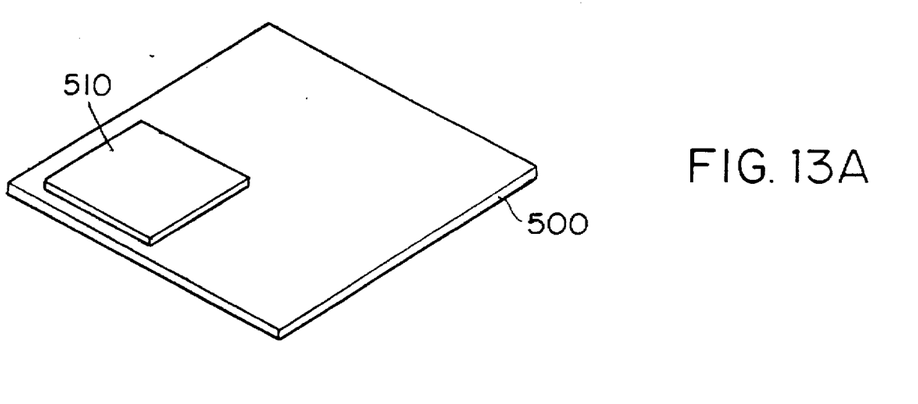
FIGS. 13A–13C illustrate a process sequence for fabricating a color filter system on an optically transmissive substrate for a liquid crystal display.
Figure 13B:
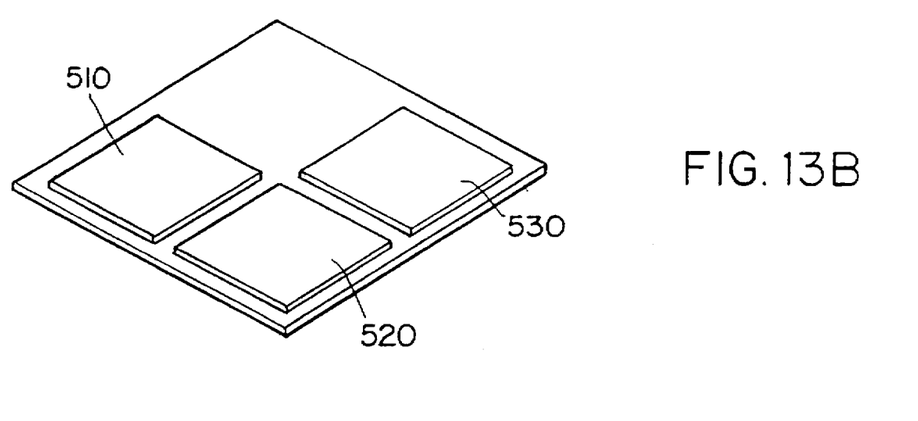
Figure 13C:
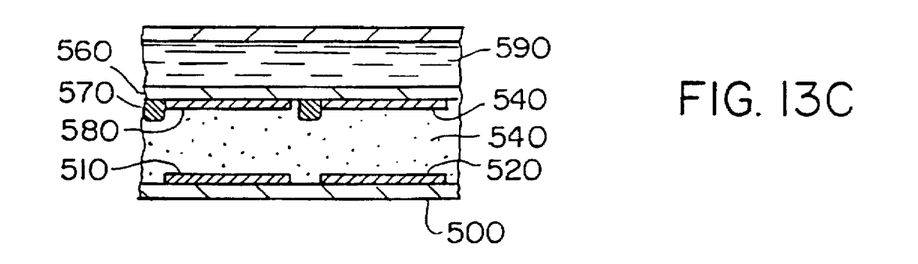

The above procedures use a process in which the color filters are placed directly on the circuit wafer before transfer. This minimizing aberrations and eliminates the need for mechanical alignment which can be particularly difficult with smaller pixel sizes. An alternative embodiment is to put the color filter system on one side of the transfer substrate such as the glass substrate 500 in a transmissive liquid crystal display as illustrated in the process sequence of FIGS. 13A–13C. Processing is the same to form the colored pixels. A formed green color filter element 510 is shown in FIG. 13A. The blue and red filter elements are then formed as shown in FIG. 13B and the circuit is then aligned with and transferred onto the color filter substrate 500 with the pixel electrodes and color filter elements bonded by an adhesive 540. After alignment the pieces are locked into place using UV cured adhesive tacks, mechanical fixture or laser spot tacking, and then oven baked to achieve the full cure on the transfer adhesive. A liquid crystal display is fabricated in accordance with this method is shown in the cross sectional view of FIG. 13C where pixel electrodes 550, 560 are separated from correlated aligned color filter elements 510, 520 by a thin adhesive layer 540 that is about 1–5 microns thick. Transistors 580 actuate the electrodes to control the transmission of light at each pixel through the liquid crystal material 590.

Figure 14A:
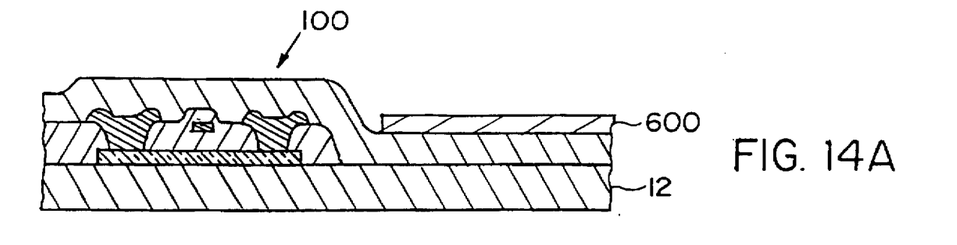
FIGS. 14A–14C illustrate a process sequence in which the color filter system and pixel electrodes are formed on opposite sides of an insulating layer.
Figure 14B:
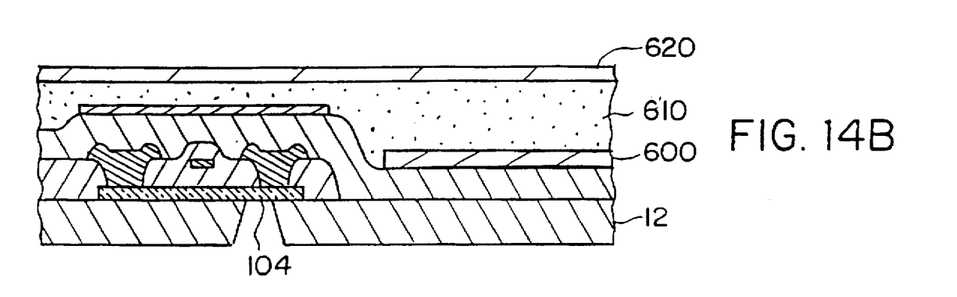
Figure 14C:
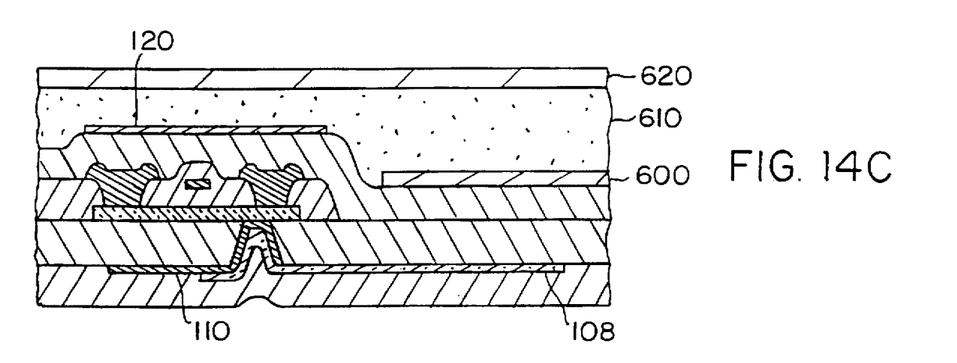

FIGS. 14A–14C illustrates a process similar to that shown in FIGS. 8A–8D, except that color filter elements 600 are fabricated after transistor 100 formation and prior to transfer and fabrication of the pixel electrodes on the opposite side of the insulator 12 (FIG. 14A). FIG. 14B shows the structure after transfer onto substrate 620 with adhesive 610 and exposure of transistor contact 104. FIG. 14C shows the device after electrode 108 formation on the opposite side of insulator 12. The electrode 108 can be formed on the opposite side of insulator 12 using the various methods previously described herein.

Figure 15:
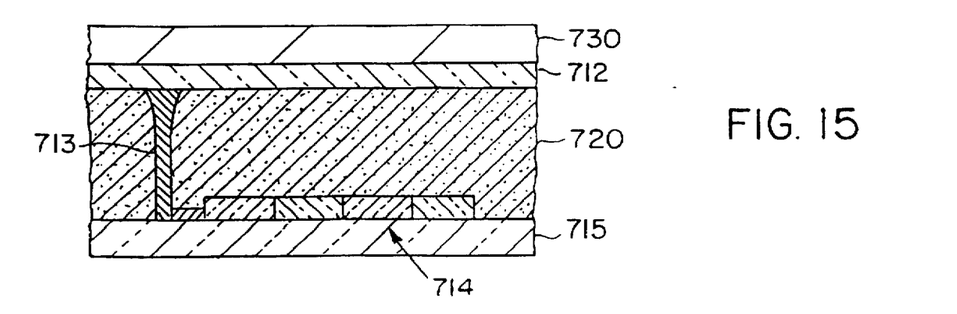
FIG. 15 is a cross sectional view of a partially fabricated display device in which electrodes are fabricated over the transistor circuits.

As display resolutions increase, the demand for real estate may increase such that the electrodes and transistors are formed in separate layers as shown in FIG. 15. As shown, a transistor circuit 714 is formed on a insulating layer 715. An insulator 720 is deposited over the transistor. An electrode 712 is formed over the insulator 720 or adhesive. The electrode 712 is interconnected to the transistor circuit 714 by an interconnect 713 through the insulator layer 720. This way, pixel elements having stacked electrodes 712 and transistors circuit 714 can be fabricated in an array of pixels. An EL stack 730 employing a white phosphor layer and color filter elements as described elsewhere herein, and in U.S. Ser. No. 07/943,896 filed on Sep. 11, 1992 which is incorporated herein by reference, are then fabricated over electrode 712, either by monolithic fabrication or transfer and alignment on a prefabricated EL stack 730 or incorporation into a liquid crystal display.

Figure 16:
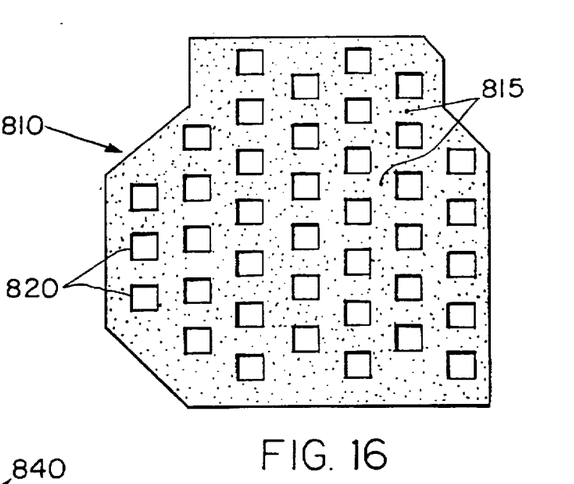
FIG. 16 is a top view of a preferred embodiment of a patterned pixel electrode.
Figure 17:
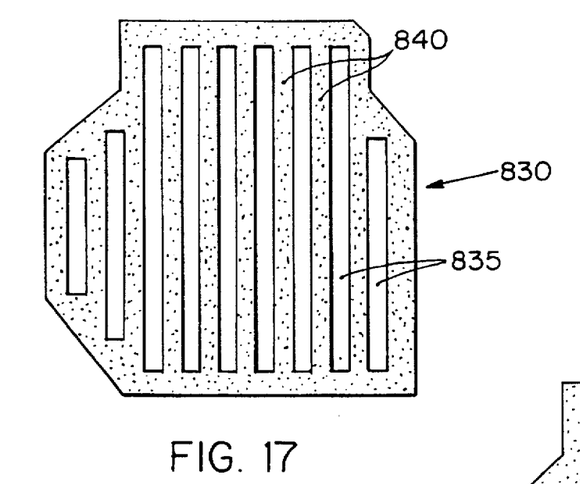
FIG. 17 is a top view of another preferred embodiment of a patterned pixel electrode.
Figure 18:
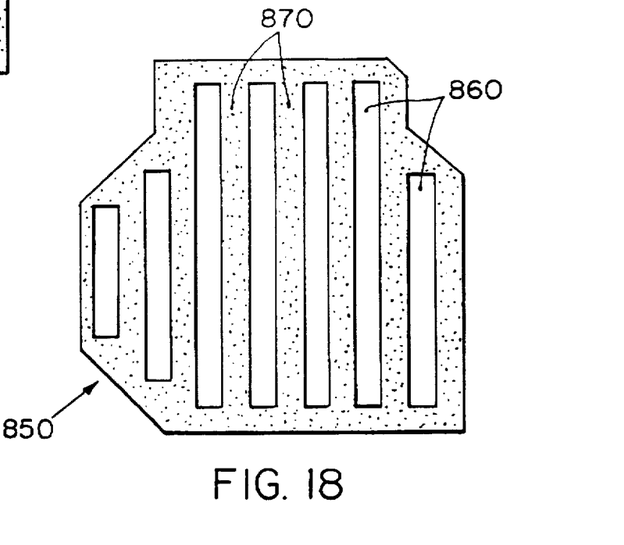
FIG. 18 it a top view of another preferred embodiment for a patterned pixel electrode.

FIGS. 16–18 are top views of patterned pixel electrodes for three preferred embodiments of an active matrix of a flat panel display. In these embodiments regions of the silicon material in an SOI structure are removed to form a pattern in each electrode. The electrode pattern can be in the form of a checkerboard pattern as shown in FIG. 16 in which an aray of separated squares have been removed, a linear grid as shown in FIGS. 17 and 18, a serpentine shape, or other suitable aperture geometry to reduce transmission loss through each pixel electrode. The individual pixel electrode 810 as shown in FIG. 16 initially comprises a solid layer of single crystal silicon. However, the element is processed such that areas 820 of silicon are removed and regions 815 of silicon remain. As shown in FIG. 17 such, the resulting pixel electrode 830 resembles a grid. The open areas 835 have a width (W1) in a range of 1–6 microns and the strips 840 of electrode material have a width (W2) of in a range of about 1–6 microns. In a preferred embodiment, there are 8–10 removed areas 835 on the pixel electrode 830. Areas 835 and strips 840 in FIG. 17 both have widths of about 2.5 microns. In FIG. 18 the pixel electrode 850 has removed areas or apertures 860 and strips 870 of electrode material that are both about 3 microns in width.

The grid provides an aperture through each pixel electrode that improves transmission of light by reducing interference effects and also reducing reflection, absorption, and scattering caused by the pixel material. One advantage of the grid-shaped pixels is the increased light transmission through the active matrix, which results in brighter displayed images. Another advantage is that grid-shaped pixels minimize thickness variations in the single crystal silicon layer. These thickness variations cause light absorption or interference, which reduces the light transmission through the active matrix. By minimizing thickness variations, brighter displayed images can be provided.

Equivalents

While this invention has been particularly shown and described with reference to preferred embodiments thereof, it will be understood by those skilled in the art that various changes in form and details may be made therein without departing from the spirit and scope of the invention as defined by the appended claims.

We claim:

1. A method of forming an active matrix display comprising:
    forming a semiconductor layer on an insulating substrate;
    forming an array of transistor circuits in the semiconductor layer;
    forming a first contact for each transistor;
    forming an array of pixel electrodes over regions of the insulating substrate from which the semiconductor layer has been removed, each pixel electrode conductively contacting a source or drain region of a transistor in each transistor circuit; and
    forming a light shield layer over the transistor circuits.

2. The method of claim 1 further comprising forming the semiconductor layer comprising single crystal silicon and forming the insulating substrate comprising forming a thin film of silicon dioxide on a silicon substrate.

3. The method of claim 2 further comprising bonding the array of pixel electrodes and transistor circuits to an optically transmissive substrate.

4. The method of claim 3 further comprising etching the silicon substrate to remove the array of transistor circuits and the array of such pixel electrodes from the substrate, the thin film insulating layer being optically transmissive.

5. The method of claim 1 further comprising forming a color filter array over the pixel electrodes.

6. The method of claim 5 wherein the color filter forming step comprises forming a polyimide film over each pixel electrode and heat treating the polyimide film.

7. The method of claim 1 wherein the pixel electrode forming step comprises forming regions of a metal oxide or a metal nitride.

8. The method of claim 1 wherein pixel electrode forming step comprises forming regions of indium tin oxide.

9. A method of forming an active matrix display comprising:
    forming a semiconductor layer on an insulating substrate;
    forming an array of transistor circuits in the semiconductor layer;
    forming an array of pixel electrodes over regions of the insulating substrate from which the semiconductor layer has been removed, each pixel electrode conductively contacting a source or drain region of a transistor in each transistor circuit; and
    forming a light shield layer over the transistor circuits.

10. The method of claim 9 further comprising forming the semiconductor layer comprising single crystal silicon and forming the insulating substrate comprising forming a thin film of silicon dioxide on a silicon substrate.

11. The method of claim 10 further comprising bonding the array of pixel electrodes and transistor circuits to an optically transmissive substrate.

12. The method of claim 11 further comprising etching the silicon substrate to remove the array of transistor circuits and the array of pixel electrodes from the substrate, the thin film insulating layer being optically transmissive.

13. The method of claim 9 further comprising forming a color filter array over the pixel electrodes.

14. The method of claim 13 wherein the color filter forming step comprises forming a polyimide film over each pixel electrode and heat treating the polyimide film.

15. A method of forming a color active matrix display comprising:
    forming a semiconductor layer on an insulating layer;
    forming an array of transistor circuits in the semiconductor layer;

forming a first contact for each transistor;

forming color filter elements over pixel electrode regions;

transferring the array of circuits and color filter elements onto an optically transmissive substrate; and subsequently forming an array of pixel electrodes over regions of the insulating substrate from which the semiconductor layer has been removed, each pixel electrode conductively contacting a source or drain region of a transistor in each transistor circuit.

16. The method of claim 15 further comprising forming the semiconductor layer comprising single crystal silicon and forming the insulating layer comprising forming a thin film of silicon dioxide on a silicon substrate.

17. The method of claim 16 further comprising bonding the array of pixel electrodes and transistor circuits to an optically transmissive substrate with an adhesive.

18. The method of claim 17 further comprising etching a silicon substrate to remove the the array of transistor circuits and the color filter elements from the substrate, the thin film insulating layer being optically transmissive.

19. The method of claim 15 wherein the color filter forming step further comprises forming an array of blue, green and red polyimide regions over each pixel electrode.

20. The method of claim 1 wherein the step of forming the array of pixel electrodes comprises forming an array of silicon electrodes.

21. The method of claim 20 further comprising depositing polycrystalline silicon to form the pixel electrodes.

22. The method of claim 1 further comprising forming the pixel electrodes in a plane extending through the array of transistor circuits.

* * * * *